United States Patent [19]

Redford et al.

[11] Patent Number: 4,900,377
[45] Date of Patent: Feb. 13, 1990

[54] METHOD OF MAKING A LIMITED LIFE PAD

[75] Inventors: Douglas E. Redford, Puyallup; Lee E. Perdelwitz, Jr., Tacoma; Ron H. Iff, Puyallup; Paul G. Gaddis; David G. Halley, both of Renton; Michael E. Cotie, Tacoma, all of Wash.; David E. Hanke, San Diego, Calif.; Amar N. Neogi, Seattle, Wash.

[73] Assignee: Weyerhaeuser Company, Tacoma, Wash.

[21] Appl. No.: 187,813

[22] Filed: Apr. 29, 1988

[51] Int. Cl.⁴ .......................... B27N 3/04; B27N 3/12
[52] U.S. Cl. ................................... 156/62.2; 156/160; 156/209; 156/251; 156/267; 156/269; 162/146; 162/157.2
[58] Field of Search .................... 604/320, 329, 385.1, 604/365-366, 369, 374, 380, 384, 387; 428/80, 288, 296, 361, 394; 128/824; 162/146, 157.2, 588, 182; 156/62.2, 160, 251, 62.6, 267, 209, 269, 290, 308.4

[56] References Cited

U.S. PATENT DOCUMENTS

| | | |
|---|---|---|
| 30,972 | 6/1882 | Kyle et al. . |
| 247,368 | 2/1878 | Whitehead . |
| 253,674 | 12/1879 | Whitehead . |
| 254,097 | 2/1880 | Richards . |
| 254,098 | 2/1880 | Richards . |
| 254,099 | 2/1880 | Richards . |
| 257,084 | 9/1880 | Fuller et al. . |
| 257,085 | 9/1880 | Fuller et al. . |
| 257,086 | 9/1880 | Fuller et al. . |
| 266,802 | 11/1882 | Gooding . |
| 272,190 | 1/1884 | Sneider . |
| 276,073 | 10/1884 | Whitehead . |
| 283,475 | 4/1886 | Reece . |
| 1,442,056 | 1/1923 | Edmonds . |
| 2,652,183 | 9/1953 | Hlivka . |
| 2,788,003 | 4/1957 | Morin . |
| 2,990,101 | 6/1961 | Mead et al. . |
| 3,016,599 | 1/1962 | Perry . |
| 3,065,751 | 11/1962 | Gobbo, Sr. et al. . |
| 3,315,676 | 4/1967 | Cooper . |
| 3,405,031 | 11/1968 | Sisson . |
| 3,427,433 | 11/1969 | Dillon ................................ 604/320 |
| 3,441,468 | 3/1969 | Siggel et al. . |
| 3,501,369 | 3/1970 | Drelich et al. . |
| 3,542,634 | 11/1970 | Such et al. . |
| 3,556,936 | 1/1971 | Miyamoto . |
| 3,570,491 | 3/1971 | Sneider . |
| 3,591,875 | 7/1971 | Zipf III et al. . |
| 3,706,626 | 2/1972 | Smith et al. . |
| 3,717,150 | 2/1973 | Schwartz . |

(List continued on next page.)

FOREIGN PATENT DOCUMENTS

| | | |
|---|---|---|
| 974107 | 9/1975 | Canada . |
| 202472A | of 0000 | European Pat. Off. . |
| 2516373 | 4/1975 | Fed. Rep. of Germany . |
| 1326915 | 11/1970 | United Kingdom . |
| 2061339 | 10/1980 | United Kingdom . |

Primary Examiner—Merrell C. Cashion, Jr.
Attorney, Agent, or Firm—Klarquist, Sparkman, Campbell, Leigh & Whinston

[57] ABSTRACT

Articles are formed of materials which have at least one layer comprising a mixture of thermoplastic and other fibers. This latter layer may be thermobonded together and then densified along at least a section of the eventual peripheral edge margin of an article to be formed from the material. Thermoplastic material containing cover sheets may also be secured to the core and densified in this manner. The entire eventual peripheral edge margin of the article is typically densified. The material is cut within the densified region or slightly outside the densified region to provide a soft peripheral edge. Absorbent materials may be thermobonded within the layer and surrounded by a densified edge to fix them within the article. The composite materials are used in manufacturing infant car seat liners and other articles. In addition, sections of the material may be densified and provided with weakened areas, such as perforations, to enable users to selectively separate the articles along the perforations.

42 Claims, 6 Drawing Sheets

U.S. PATENT DOCUMENTS

| | | |
|---|---|---|
| 3,765,997 | 10/1973 | Dunning . |
| 3,767,452 | 10/1973 | Lauchenauer . |
| 3,809,606 | 5/1974 | Stansbrey . |
| 3,877,974 | 4/1975 | Mischutin . |
| 3,881,490 | 5/1975 | Whitehead et al. . |
| 3,888,248 | 6/1975 | Moore et al. . |
| 3,891,157 | 6/1975 | Justus . |
| 3,903,890 | 9/1975 | Mesek et al. . |
| 3,927,673 | 12/1975 | Taylor . |
| 3,934,285 | 1/1976 | May . |
| 3,971,381 | 7/1976 | Gibson . |
| 3,996,825 | 12/1976 | Terry . |
| 4,047,534 | 9/1977 | Thomaschefsky et al. . |
| 4,078,124 | 3/1978 | Prentice . |
| 4,079,739 | 3/1978 | Whitehead . |
| 4,082,886 | 3/1978 | Butterworth et al. . |
| 4,100,324 | 7/1978 | Anderson et al. . |
| 4,129,132 | 12/1978 | Butterworth et al. . |
| 4,160,059 | 7/1979 | Samejima . |
| 4,170,680 | 10/1979 | Cumbers . |
| 4,182,170 | 1/1980 | Grupp . |
| 4,188,065 | 2/1980 | Meeker . |
| 4,196,245 | 4/1980 | Kitson et al. . |
| 4,213,459 | 7/1980 | Sigl et al. . |
| 4,257,842 | 3/1981 | Ciaccia et al. . |
| 4,275,105 | 6/1981 | Boyd et al. . |
| 4,286,030 | 8/1981 | Moore . |
| 4,289,580 | 9/1981 | Elston et al. . |
| 4,296,168 | 10/1981 | Ambrose . |
| 4,315,965 | 2/1982 | Mason et al. . |
| 4,333,979 | 6/1982 | Sciaraffa et al. . |
| 4,381,783 | 5/1983 | Elias . |
| 4,425,126 | 1/1984 | Butterworth et al. . |
| 4,425,130 | 1/1984 | DesMarais . |
| 4,429,001 | 1/1984 | Kolpin et al. . |
| 4,443,512 | 4/1984 | Delvaux . |
| 4,458,042 | 7/1984 | Espy . |
| 4,478,453 | 10/1984 | Schutz . |
| 4,488,928 | 2/1984 | Ali Khan et al. . |
| 4,493,868 | 1/1985 | Meitner . |
| 4,500,580 | 2/1985 | Luciani . |
| 4,525,409 | 6/1985 | Elesh . |
| 4,548,856 | 10/1985 | Ali Khan et al. . |
| 4,573,986 | 3/1986 | Minetola et al. . |
| 4,578,071 | 3/1986 | Buell . |
| 4,609,580 | 9/1986 | Rockett et al. . |
| 4,619,862 | 11/1986 | Sokolowski et al. . |
| 4,620,466 | 11/1986 | Jumel et al. . |
| 4,621,004 | 11/1986 | Madsen . |
| 4,629,457 | 12/1986 | Ness . |
| 4,647,497 | 3/1987 | Weeks . |
| 4,650,481 | 3/1987 | O'Connor et al. . |
| 4,655,877 | 4/1987 | Horimoto et al. . |
| 4,751,134 | 6/1988 | Chenoweth et al. . |
| 4,752,349 | 6/1988 | Gebel .............................. 604/385.1 |
| 4,769,023 | 9/1988 | Goebel et al. . |

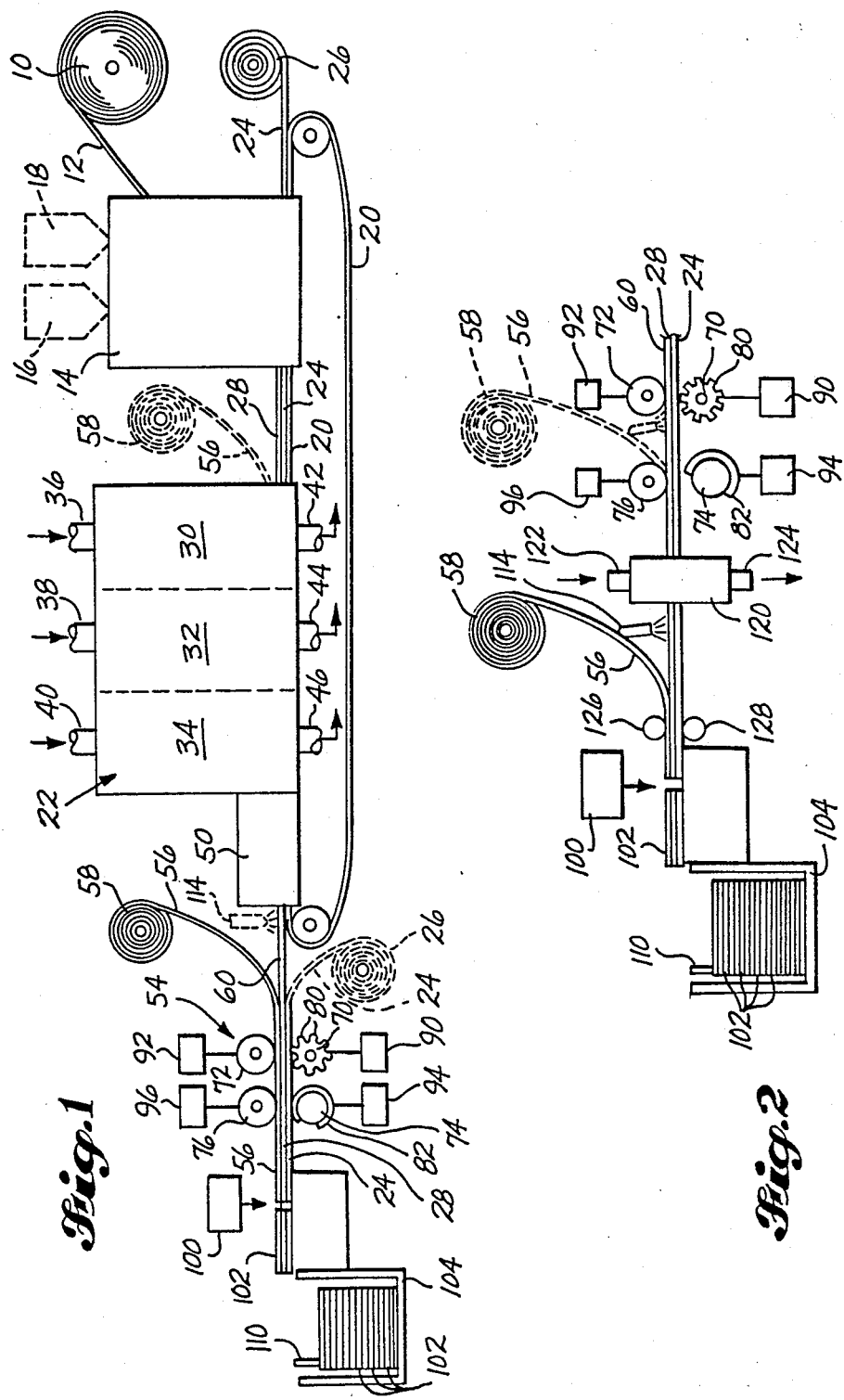

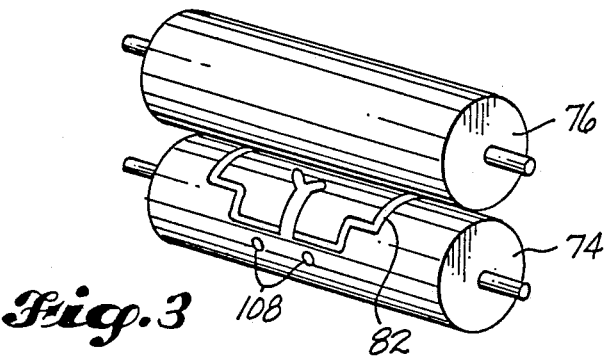
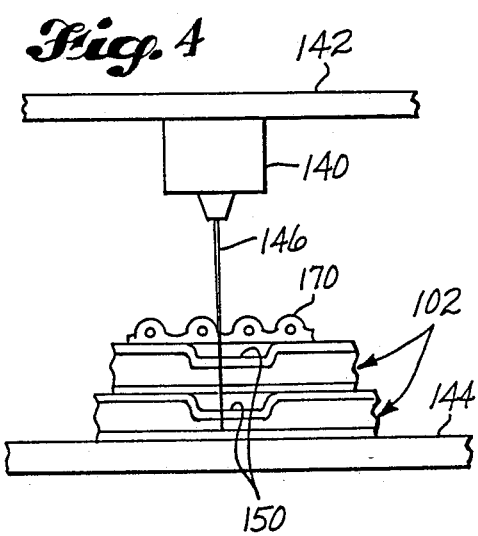
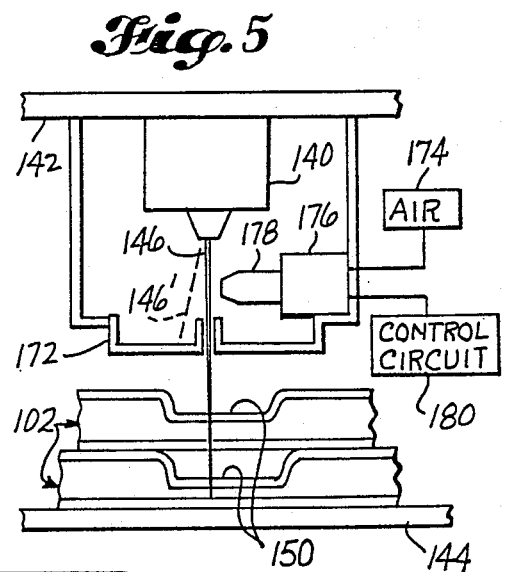
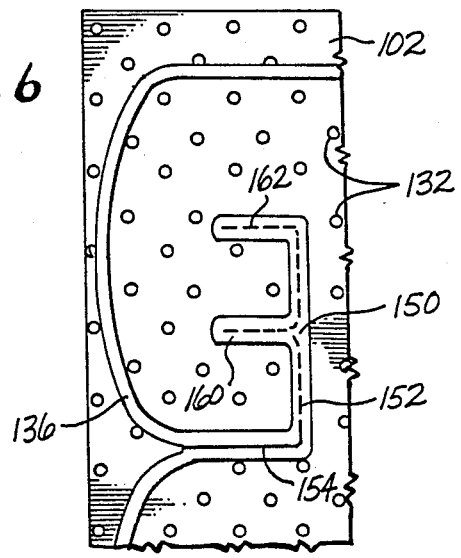

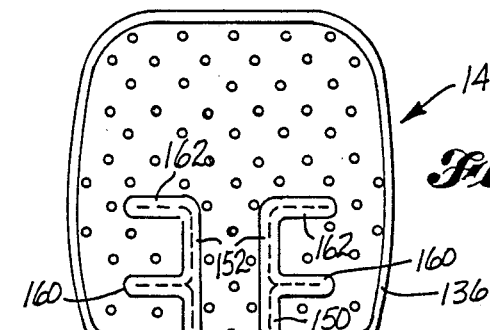
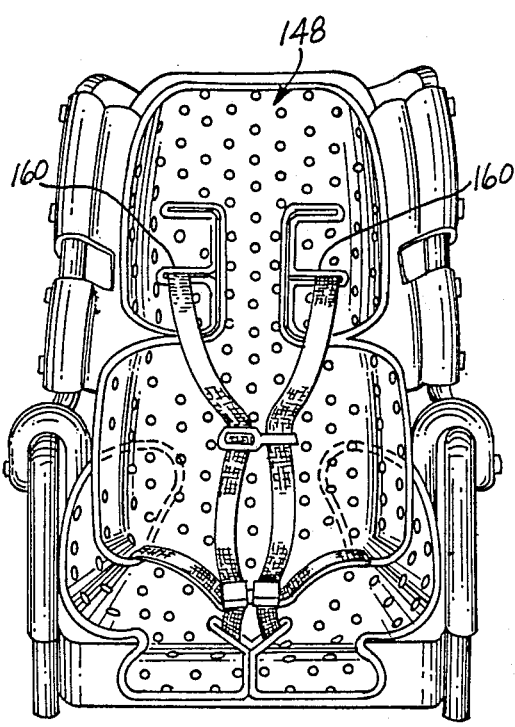
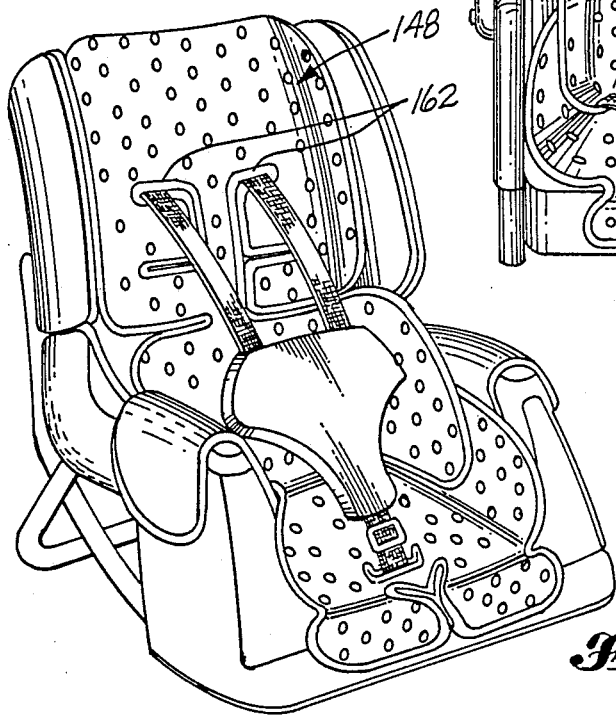

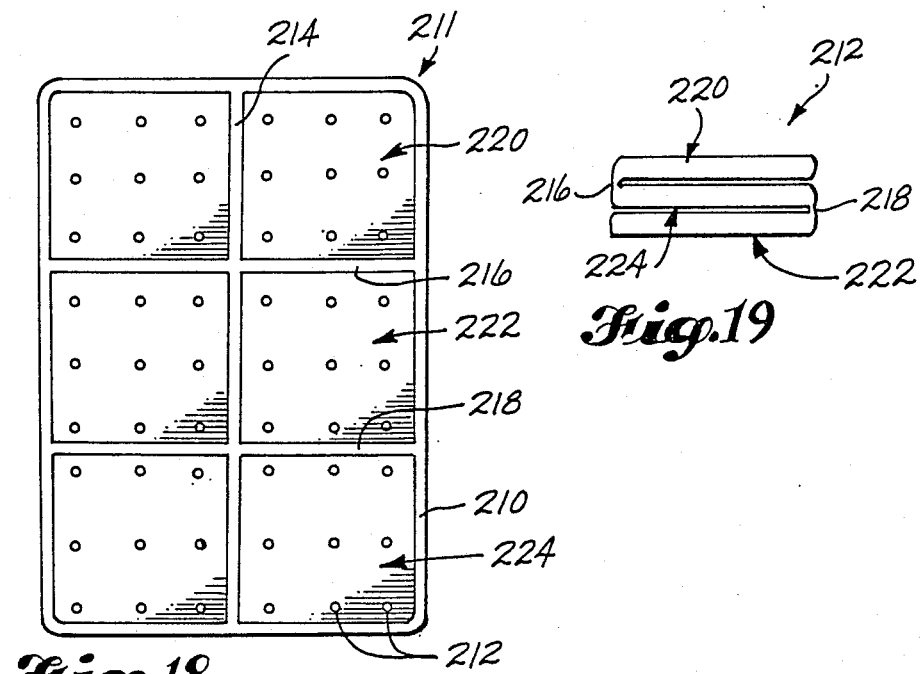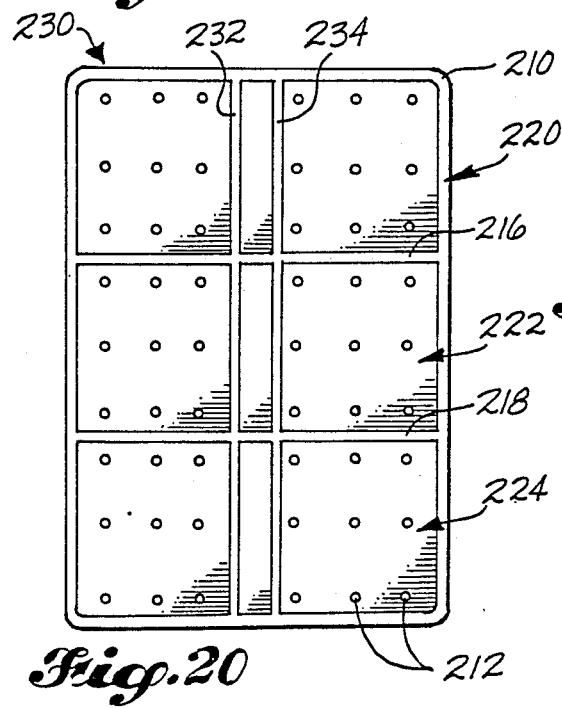

METHOD OF MAKING A LIMITED LIFE PAD

BACKGROUND OF THE INVENTION

1. Technical Field

The present invention relates to a method of making absorbent articles which contain thermoplastic materials. More specifically, the invention relates to a method of making single or multiple layer composite articles which include at least one layer formed from a mixture of thermoplastic and other nonthermoplastic fibers, such as wood pulp fibers.

2. Description Of The Prior Art

Although methods of forming articles and materials of a combination of thermoplastic and other fibers, such as wood pulp fibers, are known, these prior articles and materials produced by such methods suffer from a number of disadvantages.

U.S. Pat. No. 4,458,042 of Espy discloses an absorbent material comprised of a consolidated blend consisting essentially of wood pulp fluff and wetting agent treated spurted polyolefin pulp. The polyolefin pulp is from about 3% to about 30% of the total weight of the blend. Representative polymers for the spurted polyolefin pulps include polyethylene, polypropylene and co-polymers of ethylene and propylene. Mixtures of two or more of these polymers are also described as a suitable polyolefin pulp. The polyolefin pulp and wood pulp are blended, formed into a fluff pad and then consolidated by heating to a temperature above the melting point of the polyolefin pulp. Calenders, infrared heaters and pull-through dryers are described as representative heating devices.

Although useful, absorbent materials formed in this manner tend to lose fibers from their outer edges, particularly when shaken. In addition, pads of consolidated materials formed in this manner have a relatively low Z direction tensile strength which makes them relatively easy to pull apart, especially at the peripheral edges. Also, the method of producing pads in this manner results in pads which do not impede the leakage of liquid deposited on these materials from their outer edges.

U.S. Pat. No. 4,609,580 of Rockett et al. discloses an absorbent floor mat comprising a combination of a nonwoven liquid permeable wear surface, an absorbent inner layer of a mixture of polymeric microfibers and wood pulp, and a liquid impervious film backing layer. Intermittent bonds within the periphery or field of the floor mat are provided. These bonds are formed by a patterned application of sonic energy or heat and pressure.

In Rockett et al., a nonwoven web of nylon, such as sold under the trademark Cerex® from James River Corporation is listed as one example of a liquid permeable layer. The absorbent microfiber layer is described by Rockett et al. as being an essential feature of this mat. This layer is described preferably as an admixture of thermoplastic microfibers and "other" fibers such as wood pulp or natural or synthetic staple fibers. The absorbent layer is stated to have a basis weight in the range of from about 100-500 g/m² and preferably in the range of about 150-250 g/m². The composition of this layer is described as ranging from about 0-80% of the "other" fibers and preferably in the range of from about 60-80% wood pulp fibers by weight. The microfibers are described as preferably being of thermoplastic polymers such as polyolefins, polyesters or polyamides having a diameter on the average in the range of up to about 15 microns and preferably in the range of up to about 10 microns. Polyethylene and polypropylene microfibers are identified as specific examples.

The absorbent layer is described in this patent as preferably being formed in accordance with the "coform" process described in U.S. Pat. No. 4,100,324 of Anderson et al. In the Anderson conform approach, streams of molten polymer are deposited in an airstream and combined by a secondary air stream containing, for example, wood pulp fibers. A combination of the air streams causes the distribution of the wood pulp in the microfiber matrix. In addition, exemplary staple fibers, if included in the "other" fibers, are listed as polyester, polyolefins, polyamides and mixtures thereof. Finally, the liquid impermeable surface is described as preferably being a film with examples being thermoplastic polymers such as polyolefins, polyesters and the like, including polyethylene or polypropylene films. The film is described as being applied as a separate layer, coextruded, or coated onto the absorbent web. Calendering the exposed absorbent surface or providing a bottom adhesive layer are described as alternate ways of achieving liquid imperviousness of the underside of the floor mat.

The Rockett et al. floor mat has field bonds occupying up to about 10-25% of the surface of the floor mat. If an opened, disconnected pattern of field bonds is used, Rockett et al. discloses that up to about 20 bonds per square inch are provided. If a line pattern is used as described in Rockett et al., the pattern is up to about 10 lines per inch on the average in any direction. In use, the floor mat may be positioned in a holder which surrounds the peripheral edge of the mat.

In forming an absorbent layer in the manner of U.S. Pat. No. 4,100,324 of Anderson et al, the meltblown microfibers are softened, but are not above their melting point when they are engaged by wood pulp or the "other" fibers. Consequently, the bonding that occurs between these microfibers and the "other" fibers is relatively weak in comparison to the bonding that results when a thermobonding approach is used. Thermobonding in this sense means raising the temperature of a mixture of thermoplastic and other fibers to a temperature which is above a melt point of at least one of the thermoplastic fibers in the mixture. When this happens, a much stronger fusing of the mixture results. In addition, by relying on field bonds to secure the floor mat together, the Z direction tensile strength of the Rockett et al. composite mat is relatively weak. Moreover, the peripheral edges of the Rockett et al. floor mat are as weak as the interior areas of the mat and would not impede the leakage of liquid from these edges.

Another example of a pad which exemplifies the prior art is described in U.S. Pat. No. 4,650,481 of O'Connor et al. The pad of O'Connor et al has a liquid impermeable backing sheet, an overlaying liquid permeable face sheet and an absorbent conform layer between the backing and face sheets The interior of the pad is provided with a quilted pattern of compression lines described as being formed by ultrasonic bonding, heat and compression or the use of glue and compression. In an illustrated example, the pad is generally rectangular and the quilting lines appear to form a pattern of squares on the pad. The backing sheet is described as being generally bonded to the absorbent material by adhesive.

The coform absorbent material of the O'Connor et al. patent is described as being of meltable polymers and staple fibers formed as disclosed in U.S. Pat. No. 4,100,324 of Anderson et al. Typical polymers are described as polyethylene, polyesters, nylon and other thermoplastic fibers. Staple fibers are described as including cotton, polyester, rayon, and nylon. A combination of polypropylene meltblown fibers and wood pulp fibers is described as preferred in any desired ratio, but preferably with meltblown polypropylene fibers being present in an amount from between about 30% and about 40% by weight of the mixture. Examples of the backing sheet in O'Connor et al. include polymer films, such as copolymers of ethylene and vinyl acetate, nylon and polyesters. The preferred backing sheet films are identified in this patent as being of polyethylene or polypropylene and a composite of polypropylene and a lightweight spun bonded fabric. Spunbonded polypropylene is listed in this patent as one example of a facing sheet.

During one method of manufacturing the O'Connor, et al. pad, the facing sheet is placed on a foraminous belt with meltblown polypropylene and wood fibers being deposited onto the facing sheet as it moves below meltblown producing nozzles. The coform thus becomes mechanically attached to the facing sheet. The combined coform and facing sheet is brought in contact with an adhesively coated polymer backing sheet which is secured to the coform side of the combination. The pad is then embossed to form the quilting pattern.

The O'Connor et al. pad produced in this manner suffers from many of the drawbacks of the Rockett et al. floor mat discussed above. For example, coform provides relatively weak bonding of a pad. In addition, there is a tendency of the pad of O'Connor et al. to leak at the edges. O'Connor, et al. recognizes this and describes an embodiment (FIGS. 6 and 7) directed toward solving this problem. In this embodiment, the absorbent material is centered but does not extend completely to the peripheral edge of the pad. Instead, the facing and backing sheets are directly connected at the edge of the pad.

Therefore, although thermoplastic fibers have been combined with other fibers and used in the manufacture of articles, a need exists for improved methods for making such materials and articles.

SUMMARY OF THE INVENTION

In accordance with one aspect of the present invention, a mixture comprised of fibers of at least one thermoplastic material and other fibers, such as wood pulp fibers, is thermobonded together by heating the mixture to a temperature above the melting point of the fibers of at least one thermoplastic material in the mixture. The mixture may be deposited on a traveling foraminous belt and passed through a pull-through hot air thermobonder to supply the heat for thermobonding purposes. The resulting web or sheet is used to form pads or other articles or the core for laminated articles. The thermobonded mixture is compressed and densified along at least a section of the eventual peripheral edge margin of the article. Heat and pressure, such as supplied by embossing rolls, may be used to densify this edge section. This aspect of the invention also encompasses compressing and thermosetting or heat sealing the edges of the mixture of thermoplastic and other fibers regardless of how the remainder of the mixture is formed.

The article is then cut from the thermobonded web or sheet. The article may be severed from the web within the densified edge margin section, in which case the densified edge margin section extends to the peripheral edge of the article. Alternately, the article may be cut slightly outside of the densified edge margin section in an undensified area of the web or sheet. This produces a softer edge to the article while still maintaining the strength provided by the densified edge section. The softer edge may also be provided by perforating the outer edge of the article in the densified region. When the perforations are broken to sever the article, the resulting edge is relatively soft. The densified edge section acts as a partial liquid barrier to substantially impede the leakage of liquid across the edge section. The denser the edge section, the greater the resistance to liquid flow. Also, a pattern of discontinuous or interconnected spaced apart field bonds may be provided interiorly of the periphery of the article for added strength.

As another aspect of the present invention, absorbent materials having desired characteristics may be included in the mixture of thermoplastic and other fibers. Following thermobonding, these materials tend to be locked within the pad or core to thereby minimize the possible migration of these materials from the article. The densified edge sections also assist in retaining these materials in place and from escaping through the densified edge section of the article. As explained in greater detail below, these materials may include moisture absorbent materials such as desiccants and super absorbents, oil absorbent materials, and odor absorbent materials. Suitable materials are of the type which do not substantially degrade during thermobonding.

As described below in the detailed description, in accordance with the invention a wide variety of thermoplastic and other fibers may be included in the mixture which forms the pad, or the core in the case of composite or laminated articles. Without limiting the breadth of the invention, these mixtures may include thermoplastic fibers and wood pulp fibers in varying percentages depending upon the desired application of the material. Also, natural and synthetic staple fibers, such as cotton and rayon fibers may be included in the mixture. In addition, more than one type of thermoplastic fiber may be included in the mixture with some fibers having a melting point higher than the melting point of others. During thermobonding, these latter thermoplastic fibers are not melted, so that they retain their integrity and add to the strength of the resulting article. In addition, these latter fibers may be of a relatively long length in comparison to the other fibers for additional strength. Bicomponent thermoplastic fibers may also be included in the mixture. In addition, to enhance the blending and degree of thermobonding, wood pulp fibers may be included in the mixture which are on average generally either shorter than, or longer than, the thermoplastic fibers.

Also, the basis weight, taber stiffness, bulk and other characteristics of the articles can readily be controlled. For example, the amount of the thermobonded mixture included within the article is easily varied to adjust the basis weight. In addition, the percentage of the surface area of the field of the article which is bonded can also be varied. In accordance with the present invention, articles having extremely high basis weights and loft can be produced. These articles exhibit a high degree of tensile strength, including in the Z direction.

As a further aspect of the method of the present invention, one or more cover layers may be included with the core to provide a composite article. These cover layers may comprise thermoplastic sheet materials or webs which are thermobonded to or otherwise secured to the core. In one illustrated embodiment which is particularly well suited for infant car seat liners, the core forming fibers are deposited on a nonwoven thermoplastic facing sheet as it travels along a foraminous belt or screen. The core and facing sheet are heated to a bonding temperature sufficient to thermobond the core fibers to themselves and to the facing sheet. The integrity of the facing sheet is maintained because it has a higher melting point than the bonding temperature. A liquid impermeable backing sheet is then secured to the surface of the core opposite the facing sheet to provide a composite structure. Field bonds may be provided in the article either before or after the backing sheet is in place. The composite structure is compressed and heat sealed along the eventual peripheral edge margin of the infant seat liner and then cut as explained above. The backing sheet may be adhesively or otherwise secured at every point of contact to the core or may simply be secured at the field and peripheral bond areas. In addition, the backing sheet may be secured in place after the densified edge margin is formed. In this latter case, the backing sheet is not densified at the edge margin but is otherwise secured in place, as by adhesive.

As another aspect of the present invention, the pad, with or without cover sheets, may be densified in a region, as by the application of heat and pressure, and then weakened in such region to define a tear line. Typically, the densified and weakened region extends within the interior of an article to permit a user to selectively tear the article as desired. More specifically, the weakened areas may comprise score lines, but more preferably comprise perforations formed through the article. These perforated areas allow articles, such as infant seat liners, with optional openings to have such openings retained by the perforations closed when not needed. Also, as mentioned above, these weakened areas may also comprise perforations along a densified portion of a peripheral edge of an article to provide a soft edge when the article is separated.

As a still further aspect of the present invention, the field bonds may be formed prior to, simultaneously with, or following the densification of the edge margin of the articles. Although other approaches are suitable, preferably one or more embossing rolls are used to form the field and edge bonds. When a composite thermobonded core facing sheet is provided with field and edge bonds, the embossing rolls are preferably held at a temperature below the melting point of the thermoplastic materials of the core so as to minimize any delamination of the core and facing sheet. In addition, it has been found that a reduction in shrinkage results if the field bonds are provided prior to the peripheral edge margin bonds of an infant seat liner or other article.

Accordingly an object of the present invention is to provide improved thermoplastic containing materials and articles from such materials and improved methods for forming these materials and articles.

Still another object of the present invention is to provide methods of producing strong articles formed of thermoplastic and other fibers and in particular to provide such articles with edge sections of enhanced tear strength and which minimize leakage.

A further object of the present invention is to provide methods of efficiently manufacturing articles from thermoplastic and other fibers which can be of simple or complex shapes.

Another object of the present invention is to provide methods of manufacturing versatile materials and articles of thermoplastic and other fibers, the articles having readily controlled and variable characteristics such as varying bulks and basis weights.

Still another object of the present invention is to provide methods of forming articles of a mixture of thermoplastic and other fibers, the mixture also including optional absorbent materials such as super absorbents, oil absorbents and desiccants, the methods producing articles which minimize the risk of the escape or migration of such optional materials into the environment.

Still another object of the present invention is to provide methods of manufacturing articles of thermoplastic materials which minimize the leakage of liquids and dust from the edges of such articles.

A further object of the present invention is to provide methods of making materials of thermoplastic and other fibers and methods for making articles from such materials at a cost effective and high volume rate.

Another object of the present invention is to provide methods of making textile-like high bulk materials formed of thermoplastic and other fibers.

These and other objects, features and advantages of the present invention will become apparent with reference to the following detailed description and drawings.

BRIEF DESCRIPTION OF THE DRAWINGS

FIG. 1 is a schematic side elevational view of one form of apparatus for carrying out the present invention;

FIG. 2 is a schematic side elevational view of an alternate embodiment of a portion of the apparatus of FIG. 1;

FIG. 3 is a perspective view of a pair of embossing rolls utilized in compressing and heat sealing the peripheral edges of an article, in this case an infant seat liner, made in accordance with the present invention;

FIG. 4 is a schematic illustration of one form of apparatus used for providing weakened areas, in this case perforations, in articles made in accordance with the present invention and for cutting such articles from the material of the present invention;

FIG. 5 is a schematic illustration of an alternate embodiment of an apparatus for providing perforations in articles manufactured in accordance with the present invention and for cutting such articles from the materials of the present invention;

FIG. 6 is a top fragmentary view of a portion of an article made in accordance with the present invention;

FIG. 15 is a front view of an infant seat liner in accordance with the present invention;

FIGS. 16 and 17 illustrate the infant seat liner of FIG. 15 positioned in two different styles of infant car seats;

FIG. 18 is a front view of one form of a changing pad in accordance with the present invention;

FIG. 19 illustrates the pad of FIG. 18 after the pad has been folded;

FIG. 20 illustrates another form of changing pad in accordance with the present invention; and FIG. 21 illustrates the pad of FIG. 20 after the pad has been folded.

DETAILED DESCRIPTION OF THE PREFERRED EMBODIMENTS

Figure 9:
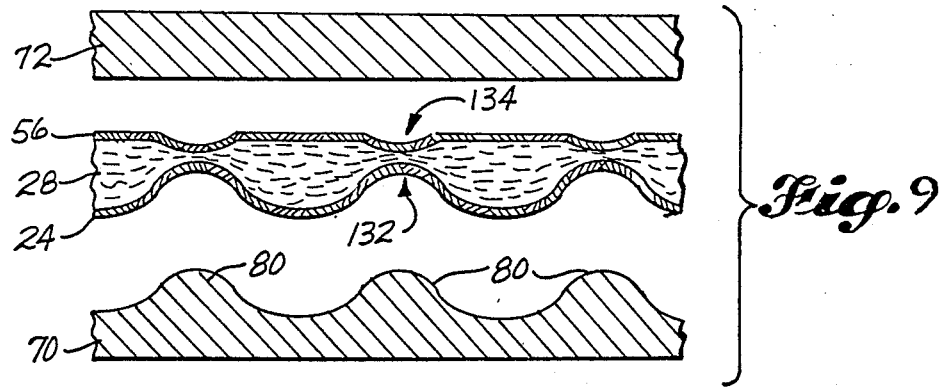
FIGS. 7 through 9 are cross-sectional views illustrating a composite material in accordance with the present invention as it enters, as it is compressed and bonded by, and as it exits from embossing rolls.

General Description of Materials Used in the Method of the Present Invention Thermoplastic Fiber Containing Core For purposes of convenience, the thermoplastic fiber containing layer will be referred to herein as a core. However, it will be appreciated that in single layer articles or two layer laminated or composite articles, the core itself respectively comprises the article either alone or with the other layer. Thus, in such cases the core would not be sandwiched between two or more cover layers.

As previously mentioned, the core is formed from a mixture of at least one thermoplastic material in fiber form in combination with one or more other fibers. These other fibers may, and preferably do, include wood pulp fibers. While not structurally as strong, it is also within the scope of the present invention to include these added materials within coform cores formed in the manner described in U.S. Pat. Nos. 4,650,481 of O'Connor et al. and 4,609,580 of Rockett et al. and densified along at least an edge section in accordance with the present invention to help retain these materials in place. These core forming fibers, on the average, have length to diameter or cross sectional dimension ratios of greater than 5 and typically have ratios close to 100.

Suitable thermoplastic fibers are typically made from thermoplastic polymers and are commercially available. These thermoplastic fibers have a high surface area to diameter ratio and are capable of melting when subjected to heat. Representative thermoplastic fibers are made from polyethylene, polypropylene, copolymers of ethylene and propylene, and copolymers of propylene and other 1-olefins such as 1-butene, 4-methyl-pentene-1, and 1-hexene. Grafted polyolefins pulps may also be used, in which maleic anhydride or styrene groups are grafted. In some embodiments, the thermoplastic fibers are composed embodiments, they are composed of mixtures of two or more types of thermoplastic fibers. Bicomponent fibers, such as comprised of polyethylene and polypropylene, may also be used. Polyester fibers are still another example of suitable fibers. Cellulose acetate is a further example of a suitable fiber.

Suitable commercially available products for making the thermoplastic fibers include Pulpex® E-338 from Hercules, Inc., a polyethylene based product; Kodel® from Eastman Kodak Corporation, a polyester based product; and Vinyon® from Celanese Corporation.

As explained in greater detail below, assume the thermoplastic materials are comprised of a mixture of more than one type of thermoplastic fibers. In this case, during thermobonding, the core is heated to a temperature sufficient to melt the lower melting point thermoplastic fibers (polyethylene) without melting the higher melting point thermoplastic fibers (polyester). Consequently, the integrity of these latter fibers is preserved and strengthens the resulting core. In addition, by making the polyester fibers of a relatively long length, such as equal to or greater than about one-half inch, cores of enhanced tensile strength are produced. Typically, in these mixtures the lower melting point thermoplastic material is included in an amount of from about 5%–85% by weight, the higher melting point thermoplastic material is included in a weight percentage of about 1%–15% by weight, and other fibers, such as wood pulp, make up the remainder of the mixture.

As previously mentioned, the fibers mixed with the thermoplastic fibers to form the core may include wood pulp. Wood pulp fibers can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, refiner mechanical, thermomechanical, chemimechanical, and chemithermomechanical pulp processes. Recycled or secondary wood pulp fibers and bleached and unbleached wood pulp fibers can be used. Details of the production of wood pulp fibers are well known to those skilled in the art. These fibers are commercially available from a number of companies, including Weyerhaeuser Company, the assignee of the present application.

In addition to wood pulp fibers, other nonthermoplastic synthetic and natural staple fibers such as rayon, cotton and the like may be included in the core forming mixture.

By making the other fibers of the mixture, such as the wood pulp fibers, either shorter on the average or longer on the average than the thermoplastic fibers, when blended the fibers of the mixture tend to become entangled to a greater extent. Therefore, upon thermobonding and melting of the thermoplastic fibers, greater contact between the thermoplastic and other fibers is achieved and stronger bonds are produced.

The optimal amount of thermoplastic and other fibers for a particular blend depends upon the bond strength and other properties desired in the final absorbent core. For cores intended to absorb aqueous based substances, thermoplastic fibers in an amount of from 5%–40% by weight and other fibers such as wood pulp in an amount of about 95%–60% by weight are suitable. In particular, blends of 80% wood pulp fibers and 20% Pulpex® have proven to be preferred. In contrast, a greater oil absorbency is achieved by increasing the thermoplastic fiber content of the mixture. For pads or cores in which this characteristic is desired, blends of thermoplastic fibers in an amount of approximately 95%–60% by weight and other fibers such as wood pulp in an amount of about 5%–40% by weight are desired.

Also, depending upon the particular application, other absorbent materials may be added to the mixture.

After the mixture is thermobonded, these added materials are substantially retained in place due to the thermobonding. The densified edge sections of the article also help retain these materials in place. Therefore, the tendency of these materials to escape or migrate from the article and into the external environment is reduced. Materials are selected which do not substantially degrade when subject to the temperature conditions that are present during thermobonding. Also, by selecting thermoplastic materials with relatively low melting points, thermobonding can be accomplished at temperatures which minimize the possible thermal degradation of these materials. Among the suitable materials that may be included in the mixture are absorbent materials such as desiccants and super absorbent materials.

In practice, any absorbent or adsorptive material can be added to the mixture. Representative examples include activated carbon, acid clay, active alumina, diatomaceous earth, silica gels and the like. Relatively newly developed superabsorbent polymers, such as cross-linked polyacrylate commercially available under the brand name "Drytech" Chemical Company may also be included. Other absorbent substances generally used in the form of a powder can conveniently be fixed in the core in accordance with the process of the present invention.

In addition, oil absorbent materials such as polymers, including polynorbornene available under the brand name "Norsorex" from C.d.F. Chemie of France, may be included. In addition, odor absorbing or deodorizing materials such as baking soda, cedar oil, and other fragrances may be included in the core forming mixture. Again, the thermobonding of the core helps fix these materials in place.

Instead of including these absorbent materials in the core forming mixture prior to bonding, they may be placed on one or both surfaces of the core following the core formation. These materials may be included in an adhesive coating on the core or simply sprayed on the core in liquid form and allowed to dry.

Finally, due to the methods of forming a core and articles of the present invention, cores of widely varying basis weights may be manufactured.

Facing Layer Materials

In the case of an article formed of the core together with one or more other layers, for convenience, one of these layers will be referred to as a facing or first covering layer.

The facing layer typically comprises a preformed sheet or web of material which travels toward a thermobonder. The facing sheet may be of a nonwoven thermoplastic containing material. The core forming mixture is deposited on the facing sheet to the desired depth. To prevent melting of the facing sheet during thermobonding, the facing sheet is selected to have a melting point which is higher than the melting point of the thermoplastic fibers of the core which are to be melted during thermobonding. When the facing sheet and deposited mixture pass through the thermobonder, the core fibers are thermobonded together and to the facing sheet. Of course, the facing sheet can be secured to the core following the formation of the core.

Thus, the selection of the facing sheet material will depend at least in part upon the thermoplastic fibers included in the core. Representative facing sheet materials include thermoplastic coated materials such as rayon which is resin or otherwise coated with a thermoplastic layer, polyolefin materials, spun laced polyester and spun bonded polyester and polypropylene, thermobonded polyester and polypropylene, carded polyester and polypropylene, melt blown polypropylene, polyethylene films of varying densities, polypropylene films, apertured films and other suitable materials apparent to those skilled in the arts.

In addition, if the illustrated manufacturing method is employed wherein heated air is pulled through the core and the facing sheet during thermobonding, the facing sheet must be perforated or otherwise breathable. Some commercially available suitable nonwoven continuous filament products include Cerex®, a nylon material from James River Corporation, Reemay®, a spun bonded polyester material from Intertec Corporation, and Sontara®, a spun laced polyester product from DuPont Corporation.

Again, a wide variety of facing sheet materials may be used. These facing sheets are thermoplastic or thermoplastic containing for those applications in which the facing sheet is to be thermobonded to the core. If the facing sheets are secured to the core in another manner, such as by adhesive, then they need not be thermoplastic. Nonwoven materials are exemplary facing sheets because such materials readily allow the passage of liquids to the absorbent core.

Backing Layer Materials

Again, for convenience, the layer of material on the opposite side of the core from the facing layer will be referred to as a backing or second cover sheet.

The backing sheet may be identical to the facing sheet and may be secured to the core during the thermobonding step. However, the backing sheet may also be comprised of a film having a melting point which is below the melting point of the thermoplastic fibers of the core which are melted during heat fusing of the core. In such a case, these materials may be secured to the core following the thermobonding step.

Also, the backing sheet materials may comprise thermoplastic materials so as to permit thermobonding or thermosetting of the backing sheet along the eventual peripheral edge margin and at field bond areas of the article. Also, the backing sheet may comprise a liquid impermeable material which assists in containing liquids absorbed by the core and through the facing sheet.

Suitable backing sheet materials include, in addition to those mentioned above in connection with the facing sheets, films of polyethylene, polypropylene and polyester and blends of these materials, linear low density polyethylene films, nylon, polyvinylchloride films and fire retardant films. An example of a commercially available suitable film is Saran® from Dow Chemical Corporation.

Thus, a wide variety of suitable materials may be used in the manufacture of thermoplastic containing articles in accordance with the present invention.

Manufacturing Method

In a typical approach, the thermoplastic and other fibers to be used in forming the core are blended by any of the known blending methods. Optional absorbent materials may also be blended in at this time. Such methods include the preparation of a pulp sheet by conventional paper-making procedures or by conventional dry blending methods. The resulting sheet is then rolled up to form a roll of core forming fibers such as indicated at 10 in FIG. 1. A sheet 12 is fed from roll 10 to a fluff preparation zone 14. At zone 14, the web 12 is formed into a fluff pad by conventional methods such as hammer milling or air forming.

In other suitable approaches, the thermoplastic core forming fibers may be fluffed separately from the other fibers, deposited in a hopper 16, and distributed by an air stream into the fluff preparation zone. In this case, the wood pulp and other fibers are similarly fluffed and deposited in a hopper 18 and distributed by an air stream within the fluff preparation zone for mixing with the thermoplastic fibers from the hopper 16. Absorbent material additives may also be added to hoppers 16 or 18. Vacuum air laying techniques may also be employed. Similarly, pulp sheets can be passed through a hammermill with the thermoplastic fibers being added in a separate step. Thus, the specific manner of forming the mixture of thermoplastic and other fibers that eventually become the core of the article is not critical.

The core forming fibers may be deposited directly on a foraminous screen 20 with the thickness of the fibers being determined in a conventional manner utilizing a doctor roll. In this case, the screen 20 carries the core forming fibers through a thermobonder 22 which heats the fibers to a temperature above the melting point of at least one thermoplastic fiber material in the core. For example, the melting point of some types of polyethylene pulp is 122° to 134° C. while the melting point of some types of polypropylene fiber is 160° to 165° C. This heat fuses the core. Although calenders, infrared heaters, and other heating devices may be employed to heat fuse the core, the illustrated thermobonder 22 comprises a flow-through dryer. The exact heating conditions, which can be readily ascertained by one skilled in the art, must be determined for the specific fiber blend being used. The time that the core spends within the thermobonder 22 is also readily ascertainable by one skilled in the art. Generally this time ranges from about one hundred milliseconds to one minute depending in part upon the temperature of the thermobonder and the line speed at which the screen is traveling. Thereafter, the core can then be densified at eventual edge margin sections of an article to be formed from the core and otherwise processed as explained below in connection with composite or laminated articles.

In the illustrated embodiment, a thermoplastic containing face sheet, such as a breathable, nonwoven, liquid permeable facing sheet web 24 from a roll 26, is positioned on screen 20 upstream from the fluff preparation zone 14. As facing sheet 24 passes through the fluff preparation zone, the core forming fibers are deposited on the facing sheet to the desired depth. The unfused core forming fibers, indicated at 28 in FIG. 1, together with the facing sheet 24, are carried by the belt 20 into the thermobonder 22.

Although not required, the thermobonder has three stages 30, 32 and 34. In each stage, heated air enters from a respective inlet 36, 38 and 40. The entering heated air passes successively through the core forming fibers 28, the facing sheet 24, the belt 20 and to a respective exit outlet 42, 44 and 46. A pressure differential is maintained across the traveling materials to draw the heated gas through these materials. For example, the inlets may be pressurized relative to the outlets or a vacuum may be applied to the outlets. The melted thermoplastic material fibers of the core 28 fuse or thermobond the core to itself and also to the face sheet 24. The temperature is such that the face sheet 24 is not melted by the thermobonder 22. Protection of the face sheet from melting is enhanced by passing heated air through the core and then to the facing sheet.

Typical line speeds for the screen 20 are from 100 to 250 feet per minute with 150 feet per minute being a normal operating speed. The thermobonder 22 includes an optional convection oven or apron 50. This oven maintains the temperature of the bonded core and facing as these materials travel toward a feature forming zone 54.

In a first approach illustrated in FIG. 1, a backing sheet 56, which may be of a thermoplastic containing liquid impermeable material, is fed from a roll 58 to the exposed surface 60 of the core.

At feature forming zone 54, the multilayered or composite web is bonded or densified along at least a section of the eventual peripheral edge margin of an article to be formed. Typically, the entire eventual peripheral edge margin of the article is densified at this time. In addition, optional field bonds may also be formed within the eventual field of the article intermediate the peripheral edge margin. A number of suitable processes may be used to form these densified areas. These include ultrasonic bonding and adhesive bonding. However, the preferred approach is to emboss these bond areas. To this end, opposed sets of embossing rolls 70, 72 and 74, 76 are positioned as shown. The illustrated roll 70 comprises a field bond feature forming roll having a projecting pattern of field bond forming contacts 80 which press against the face sheet and other layers of the composite material. Roll 72 comprises a smooth surfaced anvil roll which is positioned against the backing sheet 56. Similarly, roll 74 comprises a peripheral edge margin feature forming roll having contacts 82 arranged to define those sections of the eventual peripheral edge margins of the article which are to be densified. Normally, the entire eventual edge margin of the article is densified by feature forming roll 74. Roll 76 comprises a smooth anvil roll which backs up the feature forming roll.

A conventional temperature control 90, 92, 94 and 96 is provided for each of the respective rolls 70, 72, 74 and 76 for independently controlling the temperature of these rolls. If the same materials are being used for the backing and facing sheets, typically these rolls are kept at the same temperature. If the rolls are held at temperatures below the melting point of the thermobonding temperature of the core, the rolls are typically at 120°–130° C., depending upon the materials. In cases where the backing sheet 56 has a relatively low melting point, rolls 72 and 76 may be kept somewhat cooler (i.e. at 80–110° C. depending upon the material) than rolls 70 and 74 to act as a heat sink to assist in cooling the backing sheet 56 below its melting point.

The temperature of the embossing rolls 70 through 76 is preferably held cooler than the melting point temperatures of both the core 28 and the face sheet 24. By maintaining the core 28 above its thermobonding temperature when it reaches the embossing rolls, the feature forming rolls bring the core below the thermobonding temperature to thermoset or heat seal and compress the peripheral edge margins and field bonds in the pad or other article. Also, the core and face sheet do not tend to delaminate when embossed with these cooler embossing rolls. This helps to control the shrinkage of the article during embossing.

The field bond contacts 80 and peripheral edge margin bond contacts 82 may be placed on the same roll. When articles from some of the above described materials were made in this manner, greater shrinkage of the article resulted than when the field bonds were provided before the edge margin bonds. The peripheral bonds can be provided ahead of the field bonds. However, the preferred results were obtained when the field bonds and peripheral edge margin bonds were provided at successive embossing locations. When formed first, the field bonds reduced shrinkage and tended to keep the layers of the composite material from shifting and bunching or gathering at the peripheral edge margins of the article.

A feature roll 74 and anvil roll 76 for densifying the eventual peripheral edge margin of the infant seat liner of FIG. 15 is shown in greater detail in FIG. 3.

The nip gap between the contacts 80 and 82 and the corresponding anvil rolls is typically from about two to twelve thousandths of an inch with four to eight thousandths of an inch being preferred. Bond strength significantly decreases with a gap distance above twelve thousandths of an inch. In addition, the depth between the contact and relief portions of the feature rolls 70, 74 is sufficient to accommodate thick materials. Typically one-quarter inch to one-half inch spacing is provided between the contact and the relief portions of these rolls. Consequently, high loft, deep relief products can be produced using the FIG. 1 apparatus. Embossing pressures are variable, depending upon the desired density of the bonded areas, with 1,000 psi to 5,000 psi embossing pressures being typical.

The field embossed patterns typically comprise spaced apart embossed areas such as dots or intersecting lines. For higher bulk products, fewer field embossed areas are provided. Typically, no more than about 2%–4% of the surface of the article is embossed with field patterns. However, for some applications, additional embossing may be provided.

The Z direction tensile strength of articles formed in this manner is enhanced by the embossed areas. In addition, by embossing all or sections of the eventual peripheral edge margins of the article, the tensile strength of the article in X, Y and Z directions is substantially improved, especially at the edge. In addition, a densified peripheral edge margin impedes the leakage of liquid from the pad through the edge.

Following embossing, the articles may be separated from the composite material. Although the articles can be separated in the manufacturing line following embossing, in the illustrated embodiment the articles are separated from the composite materials at a cutting location separate from the line. Instead, a laser, die, waterknife or other cutting mechanism 100 is used to separate the composite materials into pads 102 which contain the articles defined by the peripheral edge margins embossed thereon. The separated pads 102 are then stacked in a bin 104 for subsequent transportation to a cutting zone where the finished articles are severed from the pads.

As shown in FIG. 3, optional pin register defining contacts may be included on feature roll 74. These contacts form corresponding bonds on the individual pads 102. These latter bonds may be registered with pins 110 of bin 104 so that the individual pads 102 are aligned in the bin. More than one of the aligned pads can then be cut at a time at the cutting location with the pads being held in position by pins inserted through the bonds define by contacts 108. Other pad alignment mechanisms can also be used. Also, individual pads may be cut rather than cutting the pads in stacks.

For articles with a backing sheet 56 of materials like those of face sheet 24, the backing sheet may be added to the composite material upstream of the thermobonder 22. This is shown by the roll 58 and sheet 56 depicted in dashed lines in FIG. 1. Also, the facing sheet 24 may be added following the passage of the core through the thermobonder 22. This is shown by the sheet 24 and roll 26 illustrated in dashed lines in FIG. 1. In this case, the bond between the face sheet 24 and core is not as strong as when both the core and face sheet pass through the thermobonder. Adhesive binders may be used to strengthen the bond between the face sheet and core if this approach is used.

In addition, an adhesive applicator, shown in dashed lines at 114 in FIG. 1, may be used to apply an adhesive coating to the surface 60 of the core or directly to the backing sheet ahead of the application of backing sheet 56 to the core. This adhesive serves to secure the backing sheet to the core at every point of contact between the backing sheet and core. This increases the strength of the composite material over the case where field and peripheral bonds are the only means of securing the backing sheet in place.

A wide variety of adhesive binders can be used for this purpose. For example, thermoplastic resin adhesives and aqueous latexes are suitable. These binders typically have an activation temperature in the range of from 70° to 100° C. This activation adhesive binder as the binder passes through the embossing rolls. Ethylene/vinyl/acetate copolymer is one form of suitable adhesive binder. In addition, pressure sensitive adhesives are also suitable.

In the approach illustrated in FIG. 2, the embossed thermobonded facing sheet and core is passed through a cooling chamber 120. In chamber 120, cool air is passed from an inlet 122, around the thermobonded facing sheet and core and to an outlet 124. Thereafter, adhesive is applied by applicator 114 to the surface 60 of the core. The backing sheet 56 from roll 58 is then positioned on this adhesively coated surface. The assembled composite material is then optionally pressed between a pair of rolls 126, 128 to ensure a secure bond between the backing sheet 56 and core at every point of contact between these components. Thereafter, the individual sections 102 of the material are singulated as previously described. With this approach, backing sheets of extremely low melting points may be mounted to the core without being melted by the core and while permitting high line operating speeds. In addition, glues or adhesives may be used that otherwise could be degraded by heat from the core. The adhesively secured backing sheets not only strengthen the composite material when bonded at every point of contact as previously mentioned, but also prevent propagation of tears in the backing sheet.

As another approach, the backing sheet 56 may be placed on the core between the set of field bonding rolls 70, 72 and the set of peripheral edge margin feature forming rolls 74, 76, as shown in dashed lines in FIG. 2. In this case, the sheet 56 from roll 58 is embossed at the eventual peripheral edge margin of the article but not at the field bond locations. Again, adhesive may be applied, as indicated by the applicator 114 shown in dashed lines, to the surface 60 of the core upstream of the backing sheet or applied directly to the surface of the backing sheet which is to be secured to the core.

When backing sheet 56 is comprised of a fire retardant material, such as GF19 film from Consolidated Thermoplastics, the inventors have discovered that the fire retardancy of the composite article is enhanced when the film is applied following the field bonds as shown in FIG. 2. In addition, improved bonding is provided at the peripheral edge margin of the article when the backing sheet is passed through the rolls 74, 76 in comparison to applying the backing sheet to the core downstream from these rolls.

Figure 8:
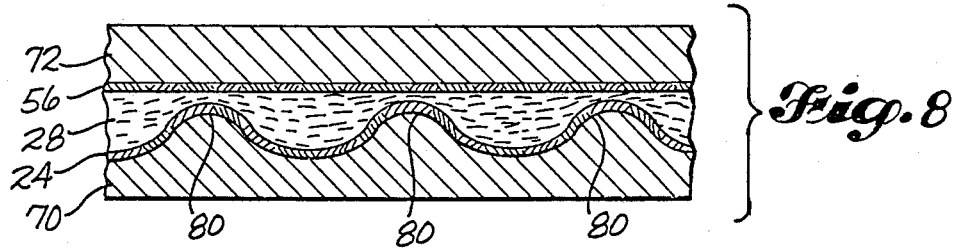
Figure 7:
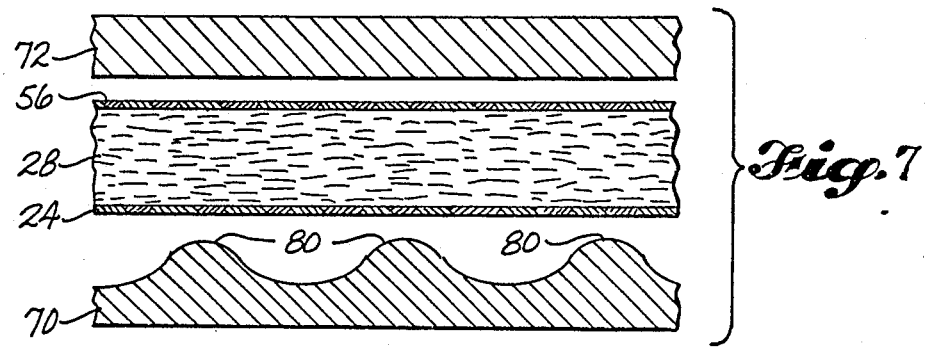

FIG. 7 depicts the composite core, facing and backing sheets as they enter the space between the rolls 70 and 72. Eventually, as shown in FIG. 8, the composite material is fully compressed between the contact points 80 of the roll 70 and the corresponding surface of the anvil roll 72. Thereafter, as shown in FIG. 9, the material passes from the field bond defining roll 70, 72 to the peripheral edge margin defining rolls 74, 76. As a result of this field bonding, compressed or dimpled areas 132 are provided in the face surface of the composite material. In addition, a slight recess 134 is typically also visible in the backing sheet due to the compression of the backing sheet during field bond formation and as a result of removal of contacts 80 from the facing surface.

Figure 10:
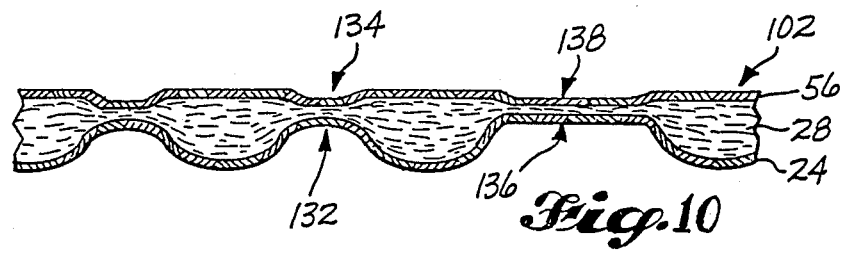
FIG. 10 is a cross-sectional view of a composite material in accordance with the present invention following the formation of field and peripheral edge margin defining bonds.

As can be seen in FIG. 10, following the densification of the eventual peripheral edge margin sections of the article, a densified area 136 remains along the eventual edge margin. Also, a slight depression 138 is present in the backing sheet opposite the depression 136. The edge margin depressions are typically one quarter to three eighths inches wide. However, interior areas of an article which are to be perforated are typically provided with slightly wider densified areas, such as areas which are about three-fourths inches wide.

At the cutting zone, the desired articles are cut from the pad sections 102 by a cutting mechanism such as a die, laser, or water knife or other cutting mechanism. Water knife cutting systems in accordance with the present invention are shown schematically in FIGS. 4 and 5. Devices using a water knife, sometimes called a fluid jet, for cutting strip-like material are known. U.S. Pat. No. 4,620,466 of Jumel et al. describes one such device. Similarly, a water knife may be used in conjunction with a cutting system sold under the brand name GerberCutter by Gerber Garment Technology, Inc. of South Windsor, Conn. With reference to FIG. 4, a water knife 140 is supported by a computer controlled movable support, such as found in the GerberCutter apparatus or the cutting machine of the aforementioned Jumel et al. patent. One or more pad sections 102 to be cut are positioned on a table 144. The table is capable of moving the pads in a direction perpendicular to the direction that the water knife is moved by support 142. This combination of motions, as described in the Jumel et al. patent and in the analogous GerberCutter system, allows any arbitrary shaped article to be cut from the pad sections 102. As previously described, the pad section 102 may be held in place by optional pins 110 (see FIG. 1). A water stream 146 from water jet 140 severs the articles.

FIG. 6 shows a pad section 102 having an infant seat liner 148 of the type shown in FIGS. 15-17 defined thereon. This particular infant seat liner, as well as other products, has a densified area 150 extending within the interior of the article. This area 150 is typically formed by feature roll 74 at the same time as the formation of the densified peripheral edge margin 136 of the article. To accommodate the shoulder straps of various types of infant car seats, the pad section 102 is provided with weakened areas that increase the manual frangibility of the article so as to permit selective user opening of the article. These areas can comprise score lines formed during die cutting of the article. However, in the illustrated embodiment, these weakened areas comprise perforations 152 formed in the article by water knife 140 as the article is severed from the pad section 102.

The entire shoulder strap receiving area of the infant seat liner 148 may be perforated, or a portion thereof, indicated at 154, may be cut entirely through the pad with the remainder being perforated as shown. By perforating the infant seat liner, the user can open the liner as required to provide access to either a first shoulder strap receiving location 160 or a second shoulder strap receiving location 162. The unopened sections of the infant seat liner 148 help to maintain the integrity of the liner. For infant car seats of the type shown in FIG. 16, perforations are opened by a user to provide access to the shoulder strap receiving locations 160. In contrast, to fit the infant car seat of FIG. 17, the perforations are opened to permit positioning of the shoulder straps of this infant seat at shoulder strap receiving locations 162.

To provide these perforations, a perforated template, such as a wire screen 170 in FIG. 4, may be positioned above the areas of the pad sections 102 which are to be perforated. As water knife 146 passes over the screen 170, the water knife is interrupted by wires of the screen to provide the perforations. The perforations are typically provided in the densified areas 150 of the pad section 102. This results in a product with a very strong edge and which resists leakage and dusting from the edge.

The FIG. 5 form of water knife cutting mechanism is similar to the FIG. 4 form. However, instead of utilizing a wire mesh 170 to form the perforations, the water jet stream 146 is deflected by air, to a position shown in dashed lines at 146' to a drainage trough 172. By repetitively deflecting and allowing the water jet stream 146 to return to its cutting position, the cutting operation is interrupted so that perforations are formed at desired locations 150 of the pad sections 102. Air for deflecting the water knife is provided by a source 174 through a valve 176 and to an air nozzle 178. The valve 176 is controlled by a control circuit 180 to open and close the valve as required to make the perforations. Other mechanical water jet deflecting mechanisms may also be used, such as deflector plates which reciprocate or otherwise move onto the path of the water jet to interrupt the jet and form the perforations. In addition, two water knives may be mounted to support 142 for cutting articles which are symmetric about a center line from the pad 102.

The outer edges of towels, infant seat liners and other articles may also be perforated in the densified regions. When severed from pads 102, fibers are pulled apart slightly along the perforations and provide a softer edge. In the case of towels or other articles, plural articles may be in a roll or on a sheet and separated by densified areas containing the perforations. The soft edge is then formed when the articles are separated, such as during manufacture or by a consumer or other user.

Figure 11:
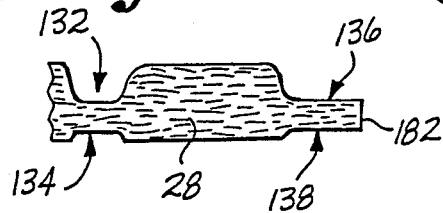
FIG. 11 is a cross-sectional view of an article of the present invention formed without cover sheets and showing the article cut in a densified edge margin section thereof.
Figure 12:
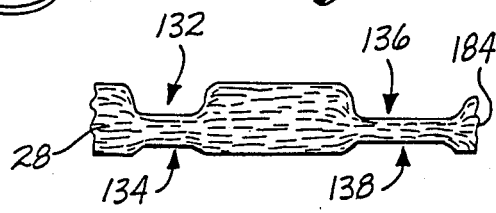
FIG. 12 is a cross-sectional view like that of FIG. 11 except that the article has been cut in an undensified area adjacent to the densified edge margin section and outside the field of the article to provide a soft edge.

As shown in FIG. 11, the cutting mechanism may be adjusted to cut the pad 102 to provide a peripheral edge 182 within the densified peripheral edge margin 136 of the pad. Alternately, as shown in FIG. 12, the cutting mechanism may be adjusted to cut the peripheral edge margin of the article at 184, a location which is slightly outside of the densified peripheral edge margin 36. For example, the peripheral edge 184 may be approximately one eighth inch away from the densified peripheral edge margin and outside of the field of the article. In this case, the peripheral edge is located in a relatively undensified area of the article. As a result, the edge will have a softer feel in comparison to the case wherein the cut is made at 182 in the densified edge margin. The cut location may be adjusted such that a soft edge is provided at selected locations along the article while a harder edge is provided at other locations. In this latter case, only selected portions of the article would have a soft edge. However, in each case, the densified peripheral edge margin strengthens the article and impedes leakage of liquids through the densified edge margin to the periphery of the article.

FIGS. 13-21 illustrate examples of various articles manufactured in accordance with the methods of the present invention. These articles are described below in connection with a number of examples. In connection with these examples, the various characteristics and properties of the thermobonded cores and of the composite articles referred to herein, and throughout the detailed description, are measured by the methods listed in Table I. In this table, ASTM refers to the American Society of Testing Materials and Tappi refers to the Technical Association of Pulp and Paper Industry.

TABLE I

| Property Measurements | | |
|---|---|---|
| Characteristics | Test Method | Units |
| Basis Weight | Tappi T-410 OM | $g/m^2$ |
| Caliper or thickness | Tappi T-411 OS | mm |
| Density | Tappi T-410 OM | $g/cm^3$ |
| Bulk | Tappi T-426 WD | cc/g |
| Machine Direction Tensile Strength | Tappi T-494 | Newtons |
| Cross Machine Direction Tensile Strength | Tappi T-494 | Newtons |
| Z Direction Tensile Strength | Tappi T-506 | $KN/m^2$ |
| Taber Stiffness | Tappi T-489 | g-cm |
| Liquid for Absorbent Capacity | ASTM-D 535 | ml/g |
| Elmendorf Tear | Tappi T-414 | Newtons |

EXAMPLE 1

In this first example, a single layer article or pad was formed by thermbonding a uniformly mixed blend or mixture of thermoplastic and other fibers of the type having a high surface area to diameter ratio. More specifically, Pulpex ® E-338 from Hercules Corporation in an amount of 20 percent by weight of the article was mixed with 80% by weight of wood pulp fibers. The specific wood pulp fibers utilized in this example were NB-316 fibers available from Weyerhaeuser Corporation. This Pulpex ® is comprised of fibers having a diameter of greater than approximately 9 microns. Fibers of this type have a greater average surface area than typically found in the case of microfibers used in coform processes. Consequently, stronger bonding results.

The mixture was deposited on the moving screen 20 (FIG. 1) and passed through the thermobonder 22, within which the thermoplastic fibers were melted to fuse the core. The fused core was also passed through a peripheral edge margin defining feature roll which densified the entire eventual edge margin of the article. Some of these pads were then cut within the densified area with a water knife so that the densified edge margin extended to the peripheral edge of the pad. These pads likewise can be cut outside of the densified area to provide a soft edge as previously described. The density at the densified edge margin has been tested at 0.3 to 0.6 $g/cm^3$ and typically can be from about 0.3 to 1.0 $g/cm^3$. The Z direction tensile strength of the pad is anticipated to be the same as the Z direction tensile strength of a multilayered pads. Thus, the dry tensile strength has been tested at 58.1 $KN/m^2$ at the densified edge margin while the wet tensile strength has been tested at 25.7 $KN/m^2$ at this location for an article with an edge margin of a density at 0.3 $g/cm^3$. Higher tensile strengths are expected for cases where the density of the edge margin is higher.

EXAMPLE 2

This example is like Example 1 with the addition of field bond areas within the field of the article. These field bond areas are spaced apart and may comprise point bonds, quilted pattern bonds, or other bond configurations. Typically, the field bonds occupy two to four percent of the surface area of the article. Pads of this type with widely varying basis weights have been manufactured in accordance with the present invention. The basis weights of pads made in this manner has ranged from eighty to seven hundred fifty $g/m^2$. In addition, by varying the quantity of the field bonds and the basis weight, pads of varying taber stiffness can be produced, such as ranging from ten to one hundred g-cm.

At the densified edge sections of the pad, the pad resists dusting or the loss of fibers at the edge and also resists leakage of liquid through the edge. Also, a pad with a densified edge can be obtained which has a good Z direction tensile strength, such as described in connection with Example 1.

Two placemats constructed in this manner were held approximately one and one-half feet over a dark piece of cloth. These placemats were rotated through three hundred sixty degrees as they were being shaken for one minute. Both placemats were then cut around their edges to eliminate the densified edge region and then shaken again in the same manner. Five individuals visually inspected the dark cloth for lint and agreed that there was no visible lint on the cloth when the uncut mats were shaken. However, they all observed a considerable quantity of lint on the cloth when the cut placemats were shaken.

EXAMPLE 3

Articles formed of thermoplastic and other fibers held together by latex bonds or coformed and provided with a thermobonded edge in accordance with the present invention also would exhibit the desired characteristics at the edge of the articles. However, in the case of coform, the Z direction tensile strength of such articles would be weaker in the body of the articles. Also, the densified edge would also be somewhat weaker unless the edge is thermobonded such as when the core is thermobonded or when the densified edge is formed.

EXAMPLE 4

In this example, the pads or articles were of a single layer comprised of a mixture of a first thermoplastic fiber of a first length which was greater than or equal to about one-half inch and present in a weight percent of from one to fifteen. In addition, a second thermoplastic fiber shorter than the first length was included within the mixture together with wood pulp fibers.

In the specific example, the first thermoplastic fibers were polyester fibers of either about one-half inch or about one inch in length, the second thermoplastic fibers were Pulpex ® fibers (polyethylene) of a shorter average length and the wood pulp fibers were kraft fibers. Comparisons were made between mixtures comprised of (a) zero percent polyester fibers, twenty percent Pulpex ® fibers, eighty percent kraft fibers; (b) five percent polyester fibers (the test being run for polyester fibers of both one-half inch and one inch in average length), fifteen percent Pulpex ® fibers and eighty percent wood pulp fibers; (c) ten percent polyester fibers (again of one-half inch and one inch average length), ten percent Pulpex ® fibers and eighty percent kraft fibers; and (d) 13.64 percent polyester fibers (again both size fibers were tested), 13.64 percent Pulpex ® fibers and 72.72 percent kraft fibers. Both plain (unembossed) and embossed pads were tested.

Table II illustrates the physical properties of the pads using wood pulp, Pulpex ® and polyester blends. As is apparent from these tables, the addition of the polyester fibers substantially increased the wet tensile strength of the pads over the examples tested without the polyester fibers.

TABLE II

PHYSICAL PROPERTIES OF PULP PADS USING PULP PULPEX ® AND POLYESTER BLENDS

| Kraft Fibers | Pulpex ® Fibers | Polyester ½" | Fiber 1" | Condition of Pad | Wet Tensile Strength (N/M) | Basis Weight (gm/m2) | Density (kg/m3) |
|---|---|---|---|---|---|---|---|
| 80 | 10 | 10 | | plain | 23.6 | 176.3 | 38.3 |
| 80 | 10 | 10 | | embossed | 22.4 | 176.6 | 44.5 |
| 80 | 10 | | 10 | plain | 20.1 | 179.6 | 39.3 |
| 80 | 10 | | 10 | embossed | 19.6 | 182.9 | 44.6 |
| 80 | 20 | 0 | | plain | 9.51 | 163.2 | 38.8 |
| 80 | 20 | 0 | | embossed | 10.9 | 164.3 | 43.3 |
| 80 | 20 | | 0 | plain | | | |
| 80 | 20 | | 0 | embossed | | | |
| 80 | 15 | 5 | | plain | 22.1 | 175.4 | 39.0 |
| 80 | 15 | 5 | | embossed | 22.5 | 118.1 | 45.4 |
| 80 | 15 | | 5 | plain | 22.4 | 178.2 | 40.4 |
| 80 | 15 | | 5 | embossed | 23.1 | 173.6 | 46.3 |
| 72.72 | 13.64 | 13.64 | | plain | 40.5 | 192.7 | 39.7 |
| 72.72 | 13.64 | 13.64 | | embossed | 34.1 | 176.7 | 48.3 |
| 72.72 | 13.64 | | 13.64 | plain | 26.8 | 181.5 | 48.4 |
| 72.72 | 13.64 | | 13.64 | embossed | 24.9 | 184.4 | 48.4 |

EXAMPLE 5

It has also been unexpectedly discovered that a combination of bicomponent synthetic fiber (such as Chori NBFH, Chori NBFI and related products) with fluff pulp at densities of from 26.5 kg/m$^3$ to 200 kg/m$^3$ have exceptional tensile strength when thermobonded. This strength is enhanced by densifying the peripheral edge of products made from these materials. These fibers also enhance hydrophilic and oleophilic properties of the finished products, depending upon the fiber used. The thermobonding is carried out at or above the melting point of the sheath polymer component but below the melting point of the core polymer component. Because of the exceptional strength of the product, the use of these bicomponent fibers provides excellent cost and performance characteristics.

EXAMPLE 6

This example is like Examples 1 and 2. In this example, it is proposed to add an absorbent material to the core forming fibers. For example, desiccants, silicon gels, or super absorbents and other previously mentioned absorbent materials may be blended with the thermoplastic and other fibers. Following thermobonding of these materials, the absorbents are effectively retained within the pad so as to minimize their escape to the external environment. In addition, oil absorbents, such as polymers including polynorbornene may be added. In addition, odor absorbents such as baking soda or deodorizers such as cedar oil may be added to the core forming materials. Cover sheets, including those containing thermoplastic materials thermobonded to the core, may also be used to enclose the cores formed in this manner. Alternately, these materials may be coated or applied as a layer on the core and held in place by adhesive and a cover layer. However, it is preferred to thermobond these materials within the core as this more effectively fixes or captures them in place. Again, by surrounding the article in whole or in part by a densified edge, added retention of these materials would be achieved.

EXAMPLE 7

In this example, the core is comprised of 20 percent Pulpex ® and 80 percent wood pulp fibers. In addition, a facing sheet of a nonwoven liquid permeable, thermoplastic material, in this case polypropylene, was used and a liquid impermeable backing sheet film, in this case polyethylene film, was used.

During manufacture, the core was thermobonded to itself and also to the face sheet in the thermobonder 22 (FIG. 1) at a temperature of about 140°–145° C. for about five seconds. The dwell time in the thermobonder is typically increased for increasing basis weight cores. In addition, the face sheet and core were thermoset together at field regions within the article and all three layers were thermoset at the eventual peripheral edge margin of the article by feature forming embossing rolls at about 120°–130° C. and anvil embossing rolls at about 80°–110° C. The article was then cut in the densified areas to form an infant seat liner as shown in FIGS. 15-17. Articles were also cut slightly outside of the densified eventual peripheral edge margin to provide a soft edge.

The basis weight of these articles varied from 80 to 450 g/m$^2$ with 150 to 300 g/m$^2$ being a preferred basis weight for infant seat liners and 200 to 250 g/m$^2$ being the ideal preferred range. The taber stiffness of the infant seat liners can be adjusted from 10 to 100 g-cm and is preferably from 20 to 50 g-cm. When positioned in an infant car seat, tested infant seat liners with a taber stiffness of from 35 to 45 g-cm tend to remain in place, although tapes or other securing mechanisms may be used to secure the liner to the infant car seat.

One specific infant seat liner constructed in this manner had a basis weight of 229.5 g/m$^2$ at its densified edge, a caliper of 0.763 mm at the edge and an edge density of 0.305 g/cm$^3$. The tensile strength of this infant seat liner at the compressed edge area of the liner in the Z direction was 58.1 KN/m$^2$ when dry and 25.7 KN/m$^2$ when wet. Ranges of tensile strength at the edge from 25 to 50 KN/m$^2$ and up when dry and from 20 KN/m$^2$ and up when wet are desired for this particular application. For reference purposes, this specific liner will be referred to as test liner A.

The density at the compressed edge area of the infant seat liner typically can be varied from 0.3 to 1.0 g/cm$^3$. In addition, although variable, the field bonds occupied an area of from about 2 to 4 percent of the entire surface of the infant seat liner.

Infant seat liners having a basis weight in the range set forth above provide good cushioning, excellent thermal insulation, good absorbency and adequate flexibility. Thermal insulation of an R value estimated at from 2 to 5 is achieved with this construction, with higher thermal insulation values being provided by higher basis weight infant seat liners. The total pad bulk of infant seat liners of this construction can typically range from 10 to 30 g/cc. In addition, the absorbency capacity of these liners has been tested at typically 10 to 16 ml/g of material. The pad wicking rate can vary from 5 to 25 ml/minute depending upon the pad construction. In addition, the tested edge wicking in ml/minute was virtually 0 in the densified edge areas of the infant seat liner for liners tested with edge densities of about 0.5 g/cm$^3$.

The tear resistance of the pad (determined in accordance with TAPPI T-414) in the machine direction varied from about 1,000 mN when no glue was used to secure the backing sheet and the backing sheet was thermoset in place to about 4,000 mN when glue was used and the backing sheet was not thermoset to the core. This tear resistance is largely a function of the thickness of the backing sheet and the temperatures to which the backing sheet has been subjected. The ratio of the wet tensile strength to the dry tensile strength of the total pad (determined in accordance with TAPPI T-494) can vary from about 0.5 to 1.0 with the same approximate ratio being present in both the machine and cross machine directions.

In addition, the Z direction tensile strength of the pad without glue being used for securing the backing sheet in place, and excluding the densified regions of the pad, can vary from about 1 to 5 KN/m$^2$.

Infant seat liners in accordance with this construction have been folded and unfolded over 5,000 times without failing. In addition, a nonwoven face sheet may be printed or otherwise provided with a decorative design. Although infant seat liners of this construction are expected to be disposable, it is anticipated that they will last from one to two months in normal use unless they become soiled. In addition, as illustrated by FIGS. 15-17, articles of very complex shapes can be produced.

EXAMPLE 8

This example is like example 7 except that the backing sheet is comprised of a fire resistant material secured to the core at every point of contact with the core, as by adhesive, after the core and facing sheet have been field bonded. More specifically, GF19 fire retardant filled polyethylene film from Consolidated Thermoplastics was used. This film has a fire resistance of less than 1, and close to 0, inches/minute when tested in accordance with the Federal Motor Vehicle Safety Standard 302. The core was comprised of 80% wood pulp fibers and 20% Pulpex ® by weight. In addition, the facing sheet comprised a carded thermobonded nonwoven polypropylene APN 185 available from James River Corporation. In this case, the core has a lower fire resistance than the backing sheet in the absence of fire retardant being included within or on the surface of the core. In addition, the basis weight of the article affects the fire resistance. With the basis weight of greater than about 200 to 250 g/m$^2$ together with the use of a fire retardant film, the composite infant seat liner of the present invention has been found to burn at less than 4 inches/minute when tested under Federal Motor Vehicle Safety Standard 302.

EXAMPLE 9

This example is like example 8 except that the backing sheet is secured in place by intermediate field bonds either with or without the adhesive. The use of field bonds and peripheral bonds increased the Z tensile strength of the composite article. However, the difference is not noticeable to any significant extent if adhesive is also used to secure the backing sheet in place. It was noticed, however, the article had a slightly lower fire resistance when the GF19 film was field bonded in this manner in comparison to the case when the film is not field bonded.

EXAMPLE 10

In this example, a pad having a non-woven back sheet and nonwoven face sheet (i.e. APN 185 nonwoven sheet material) is provided with a core having a basis weight of from 150 to 300 g/m$^2$. In addition, less than 20 bonds/inch$^2$ of the point or dot type bonds were provided. The articles of this example can have a bulk of from 10 to 30 cc/gram. The densified edge margin of the articles typically can be about 0.3 to 1.0 g/cm$^3$ as explained above. The Z direction tensile strength of these articles was above 20 KN/m$^2$ when wet at the densified edge margins and was greater than 50 KN/m$^2$ when dry at the edge margins. Moreover, the Z direction tensile strength of the articles when dry, at other than the densified edge margin, can be from 1 to 10 KN/m$^2$ depending upon the percentage of thermoplastic material included in the core. In addition, the ratio of wet to dry tensile strength of these articles was about 0.5 to 1.0. Also, the machine direction to cross machine direction dry strength ratio was less than about 2 to 1.

EXAMPLE 11

For comparison purposes, two pads were constructed under the same conditions used to produce test liner A of Example 7. The first comparison pad comprised a nonwoven face and nonwoven backing sheet (APN 185 nonwoven sheet material) with a core of 100 percent pulp fibers. The basis weight of the article was 253.2 g/m$^2$ at a densified edge of the article, the caliper of the article was 1.42 mm at the densified edge, and the density of the article at the edge was 179.5 Kg/m³. This article had a tensile strength in the Z direction at the compressed edge of 0.399 KN/m² when dry and 1.23 KN/m² when wet.

The second comparison pad was a five layer pad. In this case, from top to bottom, the pad included a top sheet of nonwoven material, a second sheet comprised of 80 percent wood pulp fibers and 20 percent Pulpex ®, a third sheet comprised of 100 percent pulp, a fourth sheet comprised of 80 percent wood pulp fibers and 20 percent Pulpex ® and a bottom sheet comprised of a non-woven material. The basis weight of this particular pad was 247.0 g/m² at the densified edge of the article, the caliper of the pad was 0.812 mm at the densified edge, and the density of the pad at the edge was 0.305 g/cm³. The tensile strength of this pad at the compressed edge in the Z direction was 11.4 KN,/m² when dry and 8.53 KN/m² when wet.

In each of these examples, the tensile strength of the article at the densified edge section is much lower than the tensile strength of articles constructed as set forth in Example 9 above.

EXAMPLE 12

Figure 14:
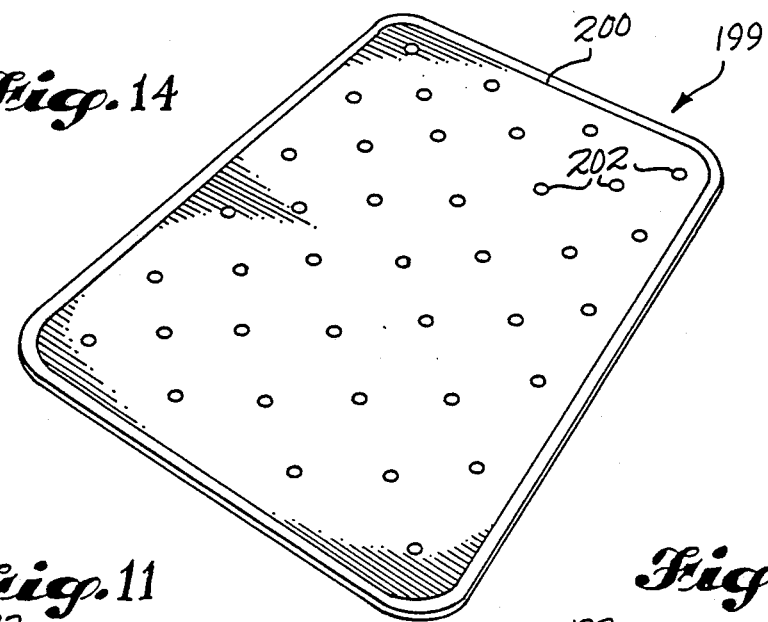
FIG. 14 is a perspective view of a towel in accordance with the present invention.

This particular example relates to the towel 199 shown in FIG. 14 which is generally of a rectangular shape. The peripheral edge of the towel is densified at 200. The edge of the towel can be perforated so that when separated from another towel, if formed in a roll, a soft edge results. In addition, point field bonds 202 are provided throughout the field of the towel. These field bonds are about 2 inches apart. The overall size of the illustrated towel is 9½ inches by 16½ inches.

This towel has a core formed of 20 percent Pulpex ® and 80 percent wood pulp fibers. In addition, a 0.7 ounce/yard non-woven thermoplastic material, in this case APN 185 carded thermobonded nonwoven polypropylene was provided as the facing and backing sheets. The facing and backing sheets are thermobonded to the core and heat sealed or thermoset at the edges.

The basis weight of the towel is approximately 175 g/m², the density of the towel is approximately 0.05 g/cm³, the taber stiffness of the towel is about 5 to 6 (and more specifically 5.4) g-cm, the thickness of the towel is about 4 mm, and the absorbency of the towel is about 10 to 15 ml/g. In addition, after being thoroughly soaked and hand wrung out, the reabsorbency of the pad, that is the ability of the towel to reabsorb moisture, was about 5 ml/g.

The towel of this construction exhibited high strength, was wringable for reabsorption purposes, and produced very little lint.

EXAMPLE 13

Figure 13:
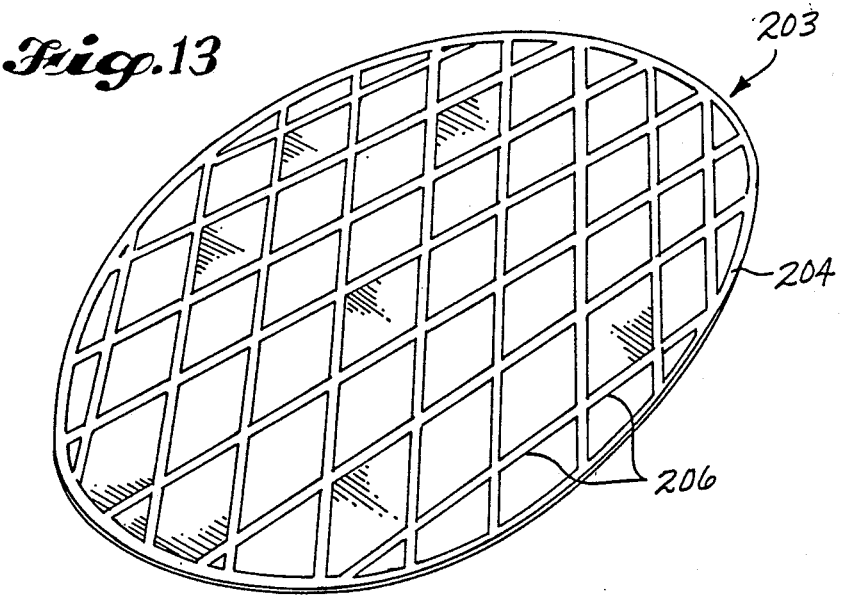
FIG. 13 is a perspective view of a mat in accordance with the present invention.

This example relates to the door mat 203 shown in FIG. 13. The mat of this example was constructed of a core comprised of 80 percent wood pulp fibers and 20 percent Pulpex ®. Facing and backing sheets comprised of 1 ounce/yard² APN 185 nonwoven thermoplastic material was used. The facing and backing sheets were thermoset to the core and densified at the periphery 204 of the mat.

The basis weight of this mat is variable, and is typically greater than 500 g/m². A specific example of this mat had a core basis weight of approximately 700 g/m². The thickness of this mat was about 12.7 mm and the density of this mat was approximately 0.05 g/cm³. The taber stiffness of this mat was approximately 250 g-cm, more specifically 254 g-cm.

The field bond areas 206 of this example pad comprise a crosshatched spaced apart diamond pattern formed of parallel bond lines extending in a first direction which are intersected by parallel bond lines extending in a second direction. The parallel lines forming this pattern are about one inch apart. The overall dimensions of the illustrated mat 203 are about 34 inches long and 24 inches wide. Although other field bonding patterns may be used, field bond patterns which form compartments within the pad surface keep the core material of the mat from shifting in the unlikely event the core material separates from the cover sheets, such as when soaked with oil or other liquid.

EXAMPLE 14

This last example relates to changing pads 211, 230 as shown in FIGS. 18-21.

Changing pads of this construction include a liquid impermeable polyethylene film backing sheet, a core formed of 80 percent wood pulp fibers and 20 percent Pulpex ® E-338, and a nonwoven liquid permeable facing sheet, such as used in Example 15.

Although variable, the basis weight of the changing pad is typically from about 100 to 200 g/m² and the density of the core of this pad is about 0.05 g/cm³. Also, the taber stiffness of the changing pad is about 25 g-cm although the taber stiffness varies with the bonding pattern employed in the pad.

In general, the illustrated changing pad is rectangular in shape. The width of the pad is about 15 inches and the length of the pad is about 23 inches. The densified periphery of the pad is about one-fourth of an inch wide. In addition, densified lines extend within the body of the pad so as to separate the pad into plural compartments These lines are elongated, that is, much longer than they are wide. These compartments minimize the leakage of liquids from the pad. In addition, the densified peripheral edge also impedes the leakage of liquids from the edge of the pad. These interior densified areas also define fold lines, enabling the folding of the pads into compact shapes. Typically, the fold lines are about one-eighth inch wide, although they are not mandatory.

Referring to FIG. 18, the changing pad 211 of this construction has a densified periphery 210 and plural point bonds 212 within the field of the article.

A first fold line 214 extends longitudinally across the center of the pad 211 and separates the pad into side by side, in this case left-hand and right-hand compartments. In addition, transverse fold defining lines, in this case at least two such lines 216, 218, extend across the changing pad in a direction normal to the fold line 214. The fold lines 216 and 218 subdivide the pad into an upper section 220, a middle section 222, and a lower section 224. When the changing pad is folded along fold line 214 and then along the fold lines 216 and 218, a folded changing pad results, as is shown in FIG. 19.

The changing pad 230 of FIG. 20 is similar to the changing pad 211 of FIG. 18. Therefore, like elements are given corresponding numbers and will not be discussed in detail. In the embodiment of FIG. 20, instead of a single longitudinally extending fold line 214, two parallel closely spaced fold lines 232, 234 are positioned parallel to and spaced equal distances from the longitudinal centerline of the pad. When the FIG. 20 changing pad is folded along fold lines 216 and 218 and then along fold lines 232 and 234, a compact package is provided as shown in FIG. 21.

Therefore, in accordance with the methods of the present invention, a wide variety of articles of varying shapes and characteristics can readily be formed from thermoplastic and other fibers.

Having illustrated and described the principles of our invention with reference to a number of preferred embodiments, it should be apparent to those of ordinary skill in the art that such embodiments may be modified in detail without departing from such principles. We claim as our invention all such modifications as come within the true spirit and scope of the following claims.

We claim:

1. A method of forcing a limited life absorbent article with a body bounded by a peripheral edge and an edge margin, the body having a field which is located interiorly of the edge margin of the body, the method comprising:
   thermobonding a mixture of thermoplastic and other fibers to form a web or sheet;
   densifying the web or sheet of fibers along a peripheral bond region extending about at least a section of the peripheral edge margin of the article to provide a substantial liquid barrier through the densified edge section.

2. A method according to claim 1 comprising the step of cutting the article from the sheet or web with the cut being positioned within the densified peripheral bond region such that the densified peripheral bond region extends to the edge of the article.

3. A method according to claim 1 comprising the step of cutting the article from the sheet or web with the cut being positioned adjacent to but outside of at least a portion of the densified peripheral bond region and outside of the field of the article such that the edge of the article which is adjacent to and outside of the peripheral bond region is of a lower density than the density of the peripheral bond region.

4. A method according to claim 1 including the step of bonding the pad together at field bond areas located in the field of the article.

5. A method according to claim 1 comprising the steps of densifying the web or sheet along a peripheral bond region extending about the entire peripheral edge margin of the article and cutting the article from the sheet or web with the cut being positioned within the densified peripheral bond region such that the densified peripheral bond region extends to the edge of the article.

6. A method according to claim 5 comprising the step of bonding the pad together at field bond areas located in the field of the article.

7. A method according to claim 1 comprising the steps of densifying the web or sheet along a peripheral bond region extending about the entire peripheral edge margin of the article and cutting the article from the sheet or web with the cut being positioned adjacent to but outside of at least a portion of the densified peripheral bond region and outside of the field of the article such that the edge of the article which is adjacent to and outside of the peripheral bond region is of a lower density than the density of the peripheral bond region.

8. A method according to claim 7 comprising the step of bonding the pad together at field bond areas located in the field of the article.

9. A method according to claim 1 in which the web or sheet comprises a core and in which the thermobonding step includes the step of thermobonding a facing sheet containing a thermoplastic material to the core, the densifying step comprising densifying the core and the facing sheet along a peripheral bond region extending about at least a section of the peripheral edge margin of the article.

10. A method according to claim 9 comprising the step of cutting the article from the sheet or web with the cut being positioned within the densified peripheral bond region such that the densified peripheral bond region extends to the edge of the article.

11. A method according to claim 9 comprising the step of cutting the article from the sheet or web with the cut being positioned adjacent to but outside of at least a portion of the densified peripheral bond region and outside of the field of the article such that the edge of the article which is adjacent to and outside of the peripheral bond region is of a lower density than the density of the peripheral bond region.

12. A method according to claim 9 including the step of bonding the pad together at field bond areas located in the field of the article.

13. A method according to claim 9 comprising the steps of densifying the web or sheet along a peripheral bond region extending about the entire peripheral edge margin of the article and cutting the article from the sheet or web with the cut being positioned within the densified peripheral bond region such that the densified peripheral bond region extends to the edge of the article.

14. A method according to claim 13 comprising the step of bonding the pad together at field bond areas located in the field of the article.

15. A method according to claim 9 comprising the steps of densifying the web or sheet along a peripheral bond region extending about the entire peripheral edge margin of the article and cutting the article from the sheet or web with the cut being positioned adjacent to but outside of at least a portion of the densified peripheral bond region and outside of the field of the article such that the edge of the article which is adjacent to and outside of the peripheral bond region is of a lower density than the density of the peripheral bond region.

16. A method according to claim 15 comprising the step of bonding the pad together at field bond areas located in the field of the article.

17. A method according to claim 9 including the step of bonding a backing sheet to the core.

18. A method according to claim 17 in which the backing sheet is adhesively bonded to the core.

19. A method according to claim 17 including the step of providing field bond areas located in the field of the article.

20. A method according to claim 19 in which the field bond areas are provided prior to forming the peripheral bond region.

21. A method according to claim 17 in which the field bond areas are provided prior to bonding the backing sheet to the core.

22. A method according to claim 21 in which the backing sheet is adhesively bonded to the core.

23. A method according to claim 17 in which the field bond areas and the peripheral bond region are provided prior to bonding the backing sheet to the core.

24. A method according to claim 23 in which the backing sheet is adhesively bonded to the core.

25. A method according to claim 24 in which the peripheral bond region extends about the entire eventual peripheral edge margin of the article.

26. A method according to claim 17 in which the backing sheet comprises a thermoplastic containing material, the densifying step comprising the step of densifying the core and the facing sheet and the backing sheet along a peripheral bond region extending about at least a section of the peripheral edge margin of the article.

27. A method according to claim 26 comprising the step of cutting the article from the sheet or web with the cut being positioned within the densified peripheral bond region such that the densified peripheral bond region extends to the edge of the article.

28. A method according to claim 26 comprising the step of cutting the article from the sheet or web with the cut being positioned adjacent to but outside of at least a portion of the densified peripheral bond region and Outside of the field of the article such that the edge of the article which is adjacent to and outside of the peripheral bond region is of a lower density than the density of the peripheral bond region.

29. A method according to claim 26 including the step of bonding the pad together at field bond areas located in the eventual field of the article.

30. A method according to claim 26 comprising the steps of densifying the web or sheet along a peripheral bond region extending about the entire peripheral edge margin of the article and cutting the article from the sheet or web with the cut being positioned within the densified peripheral bond region such that the densified peripheral bond region extends to the edge of the article.

31. A method according to claim 30 comprising the step of bonding the pad together at field bond areas located in the field of the article.

32. A method according to claim 26 comprising the steps of densifying the web or sheet along a peripheral bond region extending about the entire peripheral edge margin of the article and cutting the article from the sheet or web with the cut being positioned adjacent to but outside of at least a portion of the densified peripheral bond region and outside of the field of the article such that the edge of the article which is adjacent to and outside of the peripheral bond region is of a lower density than the density of the peripheral bond region.

33. A method according to claim 32 comprising the step of bonding the pad together at field bond areas located in the eventual field of the article.

34. A method according to claim 2 comprising the step of cutting the article with a water knife.

35. A method according to claim 3 comprising the step of cutting the article with a water knife.

36. A method of forming a limited life absorbent article with a body bounded by a peripheral edge and an edge margin comprising:
thermobonding a mixture of thermoplastic and other fibers to form a heat bonded web or sheet;
densifying the heat bonded web or sheet along a peripheral bond region extending about at least an elongated section of the peripheral edge margin while the thermoplastic material is softened by heating to fill the space between the other fibers with thermoplastic material at the densified section.

37. A method according to claim 36 in which the densifying step comprises the step of densifying the edge section sufficiently to form a substantial liquid barrier.

38. A method according to claim 36 including the steps of attaching cover sheets to the web or sheet with the web or sheet comprising a core positioned between the cover sheets.

39. A method according to claim 37 including the steps of attaching cover sheets to the web or sheet with the web or sheet comprising a core positioned between the cover sheets.

40. A method of forming a limited life absorbent article with a body bounded by a peripheral edge and an edge margin comprising:
thermobonding a mixture of thermoplastic and other fibers to form a heat bonded web or sheet;
densifying at least an elongated section of the edge margin of the web or sheet to a density of at least about 0.3 g/cc.

41. A method according to claim 40 in which the densifying step comprises the step of densifying the edge margin about substantially the entire periphery of the article.

42. A method according to claim 41 in which the densifying step comprises the step of densifying the edge margin sufficiently to provide a substantial liquid barrier through the densified edge margin.

* * * * *